United States Patent [19]

Epstein

[11] Patent Number: 5,437,657
[45] Date of Patent: Aug. 1, 1995

[54] INSTRUMENT FOR OPHTHALMOLOGICAL SURGERY

[76] Inventor: Robert L. Epstein, 1132 Michigan Ave., Wilmette, Ill. 60091

[21] Appl. No.: 107,464

[22] Filed: Aug. 16, 1993

Related U.S. Application Data

[63] Continuation of Ser. No. 939,688, Sep. 2, 1992, abandoned.

[51] Int. Cl.⁶ ............................................. A61B 17/36
[52] U.S. Cl. ........................................ 606/4; 606/5; 606/166; 606/12; 606/16
[58] Field of Search ................ 606/166, 4, 5, 6, 15, 606/16, 17, 10, 11, 12, 37

[56] References Cited

U.S. PATENT DOCUMENTS

| | | | |
|---|---|---|---|
| 3,898,840 | 8/1975 | McElroy | 73/628 |
| 4,273,127 | 6/1981 | Auth et al. | 606/16 |
| 4,627,435 | 12/1986 | Hoskin | 606/15 |
| 4,674,503 | 6/1987 | Peyman et al. | 606/166 |
| 4,705,037 | 11/1987 | Peyman et al. | 606/166 |
| 5,071,417 | 12/1991 | Sinofsky | 606/10 |

Primary Examiner—Stephen C. Pellegrino
Assistant Examiner—Sonya C. Harris
Attorney, Agent, or Firm—Merchant, Gould, Smith, Edell, Welter & Schmidt

[57] ABSTRACT

The surgical instrument apparatus emits a narrow beam of light that exits a point on the blade. The light crosses in front of the blade at a point predetermined by the surgeon. The light is reflected off the Descemet's membrane when the tip of the blade reaches the proper depth and bounces back into an entrance point on the blade. The reflected light is received by a light sensor that is coupled to a transmitter. The transmitter sends a signal to a receiver coupled to a tone generator. When the tone is generated, the surgeon knows that the incision has reached the proper depth.

15 Claims, 1 Drawing Sheet

INSTRUMENT FOR OPHTHALMOLOGICAL SURGERY

This is a continuation of application Ser. No. 07/939,688, filed Sep. 2, 1992 and now abandoned.

FIELD OF THE INVENTION

The present invention relates generally to the field of surgery and particularly to ophthalmological surgery.

Background of the Invention

The field of ophthalmological surgery has made great strides in the last few decades. Prior to the 1970's, for example, a patient suffering from myopia could typically only be treated by using corrective lenses such as glasses or contact lenses. Now, surgical techniques such as photorefractive keratecomy, keratomileusis, and radial keratotomy, also known as RK, can reduce or completely cure a patient's myopia.

RK has enjoyed the greatest growth over the past few years. This procedure is most effective on a patient requiring less than six diopters of correction. RK is performed by making four to sixteen incisions in the cornea in a spoke pattern from a central hub of untouched tissue. The number of incisions and the length and depth of each incision depends on the degree of correction that particular eye requires. A severely myopic eye would need longer and deeper incisions than a less myopic eye. The severely myopic eye would also require more incisions.

The incisions increase the surface area of the eyeball thus allowing the internal pressure of the eye to flatten the central portion of the cornea. The flattening refocuses the light entering the eye onto the retina instead of in front of it as in a myopic eye.

The RK procedure begins with a mapping of the thickness of the cornea using an ultrasound device, a procedure that is known as pachymetry. The measurements resulting from the pachymetry have an accuracy of ±1 micron. These measurements inform the surgeon on how deep the incisions can be made without perforating the cornea and entering the anterior chamber.

The surgeon then makes temporary impressions into the anesthetized eye. The impressions show where to make the incisions and where to begin and end the incising. The incising is performed by an instrument that is comprised of a blade extending through two footplates, a barrel encompasses the blade, and a micrometer on the end opposite the blade. The footplates rest on the eye while the blade is cutting. The micrometer is adjusted by the surgeon to extend or retract the blade from the end of the instrument by a predetermined amount depending on the depth of the incision required.

To achieve greater accuracy than using the micrometer alone, the blade length can be measured under the operating microscope using a scale having various depth graduations. The surgeon places the blade adjacent the depth needed on the scale and adjusts the micrometer portion of the instrument until the blade reaches that particular number. This measurement procedure has an accuracy of ±3 microns.

While incising the eye, the surgeon must maintain the depth of the incision to within 80–90% of the corneal thickness; the typical corneal thickness being 0.55 millimeter. If an incision with improper depth is made, the eye will not heal with the proper correction. Since the eye has a varying thickness, which is indicated by the pachymetry procedure, the surgeon may have to change the length of the blade for each incision to maintain the proper depth. At the same time, the RK procedure must be accomplished as quickly as possible to prevent the eye from dehydrating, thus causing the corneal thickness to change from the previously measured thicknesses. Stopping to adjust the depth of the blade slows the pace of the operation. There is a resulting need for an instrument that allows real-time feed-back to the surgeon on the depth of the blade.

SUMMARY OF THE INVENTION

The apparatus of the present invention encompasses a surgical instrument that has a blade for cutting tissue, the tissue being corneal tissue in the preferred embodiment. The apparatus is comprised of a light source that generates light to be reflected off the tissue. The reflected light is accepted by light receiving means. Alert means, that is coupled to the light receiving means, signals receipt of the reflected light. The generation of the alert signal indicates the proper depth to the surgeon.

DETAILED DESCRIPTION OF THE PREFERRED EMBODIMENT

The surgical instrument apparatus of the present invention provides real-time feed-back to the surgeon on the depth of the incision being made. By focusing a narrow beam of light at a predetermined distance from the tip of the blade and receiving the light reflected off the Descemet's membrane of the eye, an alert tone informs the surgeon when the necessary depth has been achieved.

Figure 1:
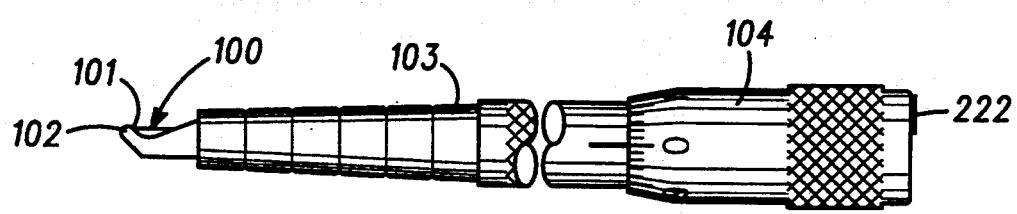
FIG. 1 shows the surgical instrument of the present invention.

The apparatus of the present invention is illustrated in FIG. 1. The apparatus, in the preferred embodiment, has a diamond blade (100). Manufacturing the blade from diamond not only allows it to be made only 150 microns thick while retaining high strength, but the optical properties of the diamond are such that light is transmitted through the blade (100).

Figure 2:
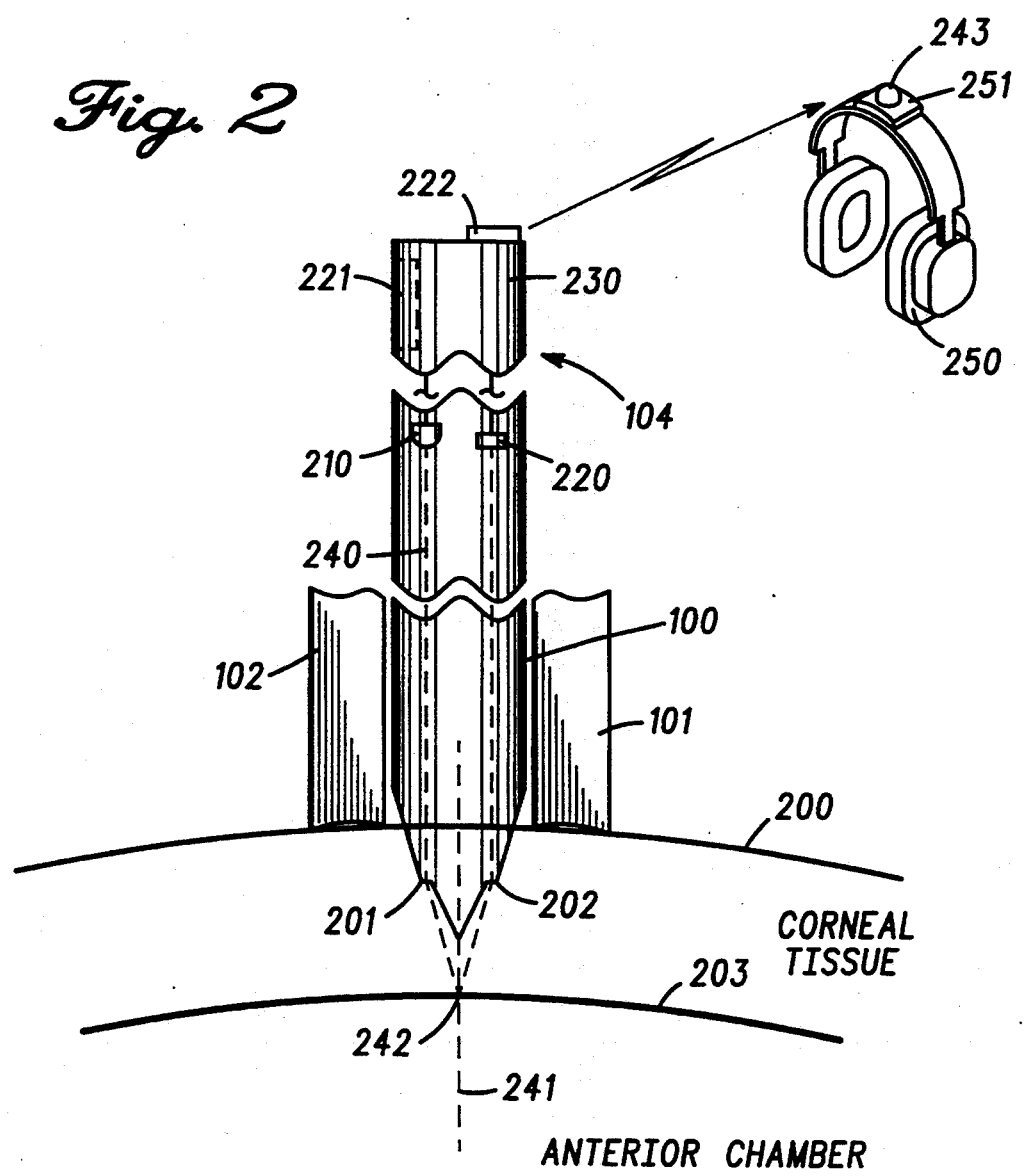
FIG. 2 shows a magnified view of the blade in association with the eye tissue to be incised.

The blade extends through two footplates (101 and 102) on either side of the blade (100). These footplates (101 and 102) rest on the eye as the surgeon is cutting. A barrel (103) encompasses the blade (100) and provides a surface for the surgeon to hold. A micrometer (104) is coupled to the end of the apparatus opposite the blade (100) end and extends or retracts the blade (100) along the apparatus's longitudinal axis, depending on the direction the micrometer is turned. Also at this end, illustrated in FIG. 2 and housed within the apparatus, is a means for generating a narrow light beam (210), a light sensor (220), light detection circuitry (230), and an infra-red light transmitter (222). The light sensor (220), detection circuitry (230), and transmitter (222) are well known in the electronics art and, therefore, will not be discussed indepth.

In the preferred embodiment, the narrow light beam (240) is generated by a laser (210). This light (240) is transmitted the length of the blade (100) and exits a notch (201) on one side of the blade. The narrow light beam (240) is angled such that it crosses, at a predetermined distance of 50 microns, a centerline (241) extending through the tip of the blade (100). In the preferred embodiment, the light beam (240) is redirected to intercept the centerline (241) by the angle that the notch is cut. In an alternate embodiment, the proper angle to intercept the centerline (241) is achieved by the placement of the laser (210) within the instrument.

As the surgeon applies pressure to the apparatus, thus causing the blade (100) to incise deeper into the corneal tissue (200), the light eventually strikes the shiny surface of the Descemet's membrane (203). The light striking (242) this surface signals the proper depth of the incision. The light is reflected off the membrane (203) and back into the blade (100) through another notch (202) cut into the blade (100) opposite the light exit point (201). This light entrance notch (202) is formed such that the narrow beam of entering light is transmitted up the length of the blade (100).

The light sensor (220) in the micrometer end (104) of the apparatus receives the light. This sensor (220), in combination with the light detection circuitry (230), transforms the light energy into a current that is detected by the transmitter (222). In the preferred embodiment, the transmitter (222) transforms the current into an infra-red signal for transmission to an infra-red receiver (243) mounted in headphones (250) worn by the surgeon. Tone generation circuitry (251) is contained in the headphones (250) to emit a tone to inform the surgeon that the proper depth has been achieved.

An alternate embodiment uses radio frequencies instead of the infra-red to transmit the correct depth reached signal. Another embodiment mounts the tone generation circuitry on the apparatus to generate an alert that is heard without;the use of headphones. Yet another embodiment of the present invention would mount the laser on one of the footplates, angled such that the light beam intersects the centerline. The light sensor is mounted on the opposing footplate to receive the reflected light beam.

If, in an alternate embodiment, a blade is used that does not have light conducting properties, such as stainless steel, a light conducting coating can be applied to each side of the blade. The coating would end just above the tip of the blade, thus forming a light exit point on one side and a light entrance point on the other. The laser would then be positioned at the other end of one of the coatings to transmit the narrow light beam the length of the coating and out the light exit point. The other coating would then receive the reflected light and transmit it back to the light sensor.

Using the surgical apparatus of the present invention, a surgeon can cut corneal tissue to the proper depth without constantly measuring the length of the blade. By reflecting light off the Descemet's membrane at a distance from the tip of the blade to assure proper incision depth, the surgeon has real-time feed-back on the depth of the incision.

I claim:

1. A surgical instrument for cutting tissue, the instrument comprising:
   (a) a blade having a first side, a second side, and light conducting capability, the blade having a light exit point located on the first side and a light entrance point located on the second side;
   (b) a light source substantially aligned with the light exit point such that light from the light source exits the light exit point;
   (c) a light sensor substantially aligned with the light entrance point such that the light from the light exit point, that is reflected into the light entrance point, will contact the light sensor; and
   (d) an alert generator, operatively coupled to the light sensor, for signaling receipt of the reflected light.

2. The instrument of claim 1 wherein the light exit point and the light entrance point each comprise notches in the blade, the light exit point being angled such that the light exiting the light exit point intercepts a centerline of the blade.

3. A surgical instrument system for cutting corneal tissue, the apparatus comprising:
   (a) a light conducting blade having a first side and a second side, a light exit point located on the first side and a light entrance point located on the second side;
   (b) a laser for generating light that exits the light exit point;
   (c) a light sensor, substantially aligned with the light entrance point, for receiving light reflected by the corneal tissue into the light entrance point, the light sensor generating a depth reached signal in response to the received reflected light;
   (d) a transmitter, coupled to the light sensor, for transmitting the depth reached signal;
   (e) a receiver for receiving the depth reached signal; and
   (f) a tone generator, operatively coupled to the receiver, for generating a tone in response to the received depth reached signal.

4. The apparatus of claim 3 wherein the transmitter comprises means for transmitting infra-red light.

5. The apparatus of claim 3 wherein the transmitter comprises means for transmitting radio frequency signals.

6. A surgical instrument for cutting a first tissue to a depth such that a second, light reflecting tissue is substantially exposed, the instrument comprising:
   (a) a blade having a tip and a centerline extending through the tip of the blade;
   (b) a light source that emits light means to reflect the light such that the light intercepts the centerline and angularly reflects off the second tissue;
   (c) a light sensor for receiving the reflected light; and
   (d) an alert generator, coupled to the light sensor, for signaling receipt of the reflected light.

7. A surgical instrument, comprising:
   (a) a blade means for cutting tissue, the blade means having a blade tip and a centerline extending through the blade tip;
   (b) a light source that emits light means to reflect the light such that the light intercepts the centerline;
   (c) a light sensor for receiving light angularly reflected from light reflecting tissue; and
   (d) an alert generator, operatively coupled to the light sensor, for signaling receipt of the reflected light.

8. The surgical instrument of claim 7 wherein the blade means comprises means for cutting.

9. The surgical instrument of claim 7 wherein the blade means comprises means for cutting corneal tissue.

10. The surgical instrument of claim 7 wherein:
   (a) the blade means comprises a light conducting blade having a first side and a second side, the blade comprising a light exit point located on the first side of the blade and a light entrance point located on the second side of the blade;

(b) the light is substantially aligned with the light exit point such that light from the light source exits the light exit point; and (c) the light sensor is substantially aligned with the light entrance point such that light which exits the light exit point and is reflected by the reflecting tissue may enter the light entrance point and contact the light sensor.

11. The surgical instrument of claim 10 wherein the light exit point and the light entrance point each comprise a notch in the blade, the light exit point being angled such that the light exiting the light exit point intercepts the centerline extending through the blade tip.

12. The surgical instrument of claim 7 wherein the light source comprises a laser.

13. The surgical instrument of claim 7:
(a) wherein the light sensor comprises depth sensing means for generating a depth reached signal in response to the received reflected light; and
(b) the alert generator comprises means for generating a tone in response to the depth reached signal.

14. The surgical instrument of claim 7:
(a) wherein the alert generator is operatively coupled to the light sensor through a communication link;
(b) further comprising a transmitter, operatively coupled to the light sensor, for transmitting the depth reached signal via the communication link; and
(c) further comprising a receiver for receiving the depth reached signal via the communication link.

15. The surgical instrument of claim 14 wherein the communication link is selected from the group consisting of: an infra-red light link, a radio frequency link, and a wireline link.

* * * * *

UNITED STATES PATENT AND TRADEMARK OFFICE
CERTIFICATE OF CORRECTION

PATENT NO. :   5,437,657

DATED      :   August 1, 1995

INVENTOR(S) :  Epstein

It is certified that error appears in the above-identified patent and that said Letters Patent is hereby corrected as shown below:

In column 3, line 34, delete ";" after the word "without".

In column 4, line 62, claim 8, insert --a first tissue to a depth such that a light reflecting second tissue is substantially exposed-- after the word "cutting".

Signed and Sealed this

Sixteenth Day of January, 1996

Attest:

BRUCE LEHMAN

*Attesting Officer*   *Commissioner of Patents and Trademarks*